United States Patent
Shiba et al.

(10) Patent No.: US 10,955,410 B2
(45) Date of Patent: Mar. 23, 2021

(54) METHOD OF RECOVERING EXTRACELLULAR VESICLES AND CONTAINER FOR EXTRACELLULAR VESICLES

(71) Applicants: JAPANESE FOUNDATION FOR CANCER RESEARCH, Tokyo (JP); NOF CORPORATION, Tokyo (JP)

(72) Inventors: Kiyotaka Shiba, Tokyo (JP); Nobuyuki Sakamoto, Kanagawa (JP); Tomozumi Noda, Kanagawa (JP); Satoshi Yamada, Kanagawa (JP)

(73) Assignees: JAPANESE FOUNDATION FOR CANCER RESEARCH, Tokyo (JP); NOF CORPORATION, Tokyo (JP)

( * ) Notice: Subject to any disclaimer, the term of this patent is extended or adjusted under 35 U.S.C. 154(b) by 52 days.

(21) Appl. No.: 16/303,798

(22) PCT Filed: May 23, 2017

(86) PCT No.: PCT/JP2017/019121
§ 371 (c)(1),
(2) Date: Nov. 21, 2018

(87) PCT Pub. No.: WO2017/204187
PCT Pub. Date: Nov. 30, 2017

(65) Prior Publication Data
US 2020/0025750 A1 Jan. 23, 2020

(30) Foreign Application Priority Data
May 24, 2016 (JP) .............................. JP2016-103091

(51) Int. Cl.
- G01N 33/543 (2006.01)
- C08F 20/28 (2006.01)
- C08F 230/02 (2006.01)
- C09D 133/14 (2006.01)
- C09D 143/02 (2006.01)

(52) U.S. Cl.
CPC .......... *G01N 33/543* (2013.01); *C08F 20/28* (2013.01); *C08F 230/02* (2013.01); *C09D 133/14* (2013.01); *C09D 143/02* (2013.01)

(58) Field of Classification Search
CPC .................................................. G01N 33/543
See application file for complete search history.

(56) References Cited

U.S. PATENT DOCUMENTS

| 6,899,863 B1 | 5/2005 | Dhellin et al. |
|---|---|---|
| 9,434,858 B2 | 9/2016 | Matsuoka et al. |
| 2006/0252148 A1 | 11/2006 | Kurosawa et al. |
| 2012/0097169 A1 | 4/2012 | Tei et al. |
| 2014/0031256 A1 | 1/2014 | Lim |
| 2016/0169876 A1 | 6/2016 | Ichiki et al. |
| 2016/0349246 A1 | 12/2016 | Fujii et al. |

FOREIGN PATENT DOCUMENTS

| CN | 104812857 | | 7/2015 | |
|---|---|---|---|---|
| EP | 1152242 | A1 | 11/2001 | |
| JP | H07-005177 | A | 1/1995 | |
| JP | H07-83923 | | 3/1995 | |
| JP | 2002-535665 | | 10/2002 | |
| JP | 2003-531864 | | 10/2003 | |
| JP | 2004-275862 | A | 10/2004 | |
| JP | 2005-099040 | A | 4/2005 | |
| JP | 2005099040 | A * | 4/2005 | |
| JP | 2014-507140 | | 3/2014 | |
| WO | 01/82958 | A2 | 11/2001 | |
| WO | 2005/001019 | A1 | 1/2005 | |
| WO | 2015/029979 | A1 | 3/2015 | |
| WO | 2015/068772 | A1 | 5/2015 | |
| WO | WO-2016033695 | A1 * | 3/2016 | ........... A61K 9/5184 |

OTHER PUBLICATIONS

T Akagi, K Kato, M Kobayashi, N Kosaka, T Ochiya, T Ichiki. "On-Chip Immunoelectrophoresis of Extracellular Vesicles Released from Human Breast Cancer Cells." Plos One, vol. 10(4), e0123603, pp. 1-13, published Apr. 30, 2015. (Year: 2015).*
K Ishihara, H Oshida, Y Endo, T Ueda, A Watanabe, N Nakabayashi. "Hemocompatibility of human whole blood on polymers with a phospholipid polar group and its mechanism." Journal of Biomedical Materials Research, vol. 26, 1992, pp. 1543-1552. (Year: 1992).*
Y Hamada, T Ono, T Akagi, K Ishihara, T Ichiki. "Photochemical Oxidation of Poly(dimethylsiloxane) Surface and Subsequent Coating with Biomimetic Phosphorylcholine Polymer." Journal of Photopolymer Science and Technology, vol. 20 No. 2, 2007, pp. 245-249. (Year: 2007).*

(Continued)

*Primary Examiner* — Isaac Shomer
(74) *Attorney, Agent, or Firm* — Rankin, Hill & Clark LLP (57) ABSTRACT

A coating agent for preventing the adsorption of extracellular vesicles represented by exosomes to a tool has been developed. Adsorption of extracellular vesicles to a tool can be prevented by using a coating agent which contains a hydrophilic polymer having a weight average molecular weight of 10,000 or more and 1,000,000 or less, wherein a coated layer formed by the coating agent has a contact angle of 0 degree or more and 30 degrees or less.

1 Claim, 5 Drawing Sheets

(56) References Cited

OTHER PUBLICATIONS

English Translation of JP 2005099040 A. Obtained from Google Translate at https://patents.google.com/patent/JP2005099040A/en?oq=JP+2005-099040 on Mar. 10, 2020. Originally published in Japanese on Apr. 14, 2005. 6 printed pages. (Year: 2005).*

N Yamamoto, H Irie, N Sakamoto, K Shuto, T-A Yamagishi, Y Nakamoto. "Self-aggregates of Highly Hydrophobic Phospholipid Polymers in Aqueous Solution." Journal of Oleo Science, vol. 55 No. 9, 2006, pp. 465-471. (Year: 2006).*

Zheng Zhao, Yang Yang, Yong Zeng and Mei He. "A microfluidic ExoSearch chip for multiplexed exosome detection towards blood-based ovarian cancer diagnosis." Lab on a Chip, vol. 16, 2016, pp. 489-496, published online Nov. 20, 2015. (Year: 2015).*

Clotilde Thery, Aled Clayton, Sebastian Amigorena, and Graca Raposo. "Isolation and Characterization of Exosomes from Cell Culture Supernatants and Biological Fluids." Current Protocols in Cell Biology, (2006) pp. 3.22.1-3.22.29. (Year: 2006).*

Kazuya Iwai, Satoshi Yamamoto, Mitsutaka Yoshida, and Kiyotaka Shiba. "Isolation of Extracellular Vesicles in Saliva Using Density Gradient Ultracentrifugation." Chapter 27, Extracellular Vesicles: Methods and Protocols, Methods in Molecular Biology, vol. 1660, 2017, pp. 343-350. (Year: 2017).*

E.I. Trilisky, A.M. Lenhoff. "Sorption processes in ion-exchange chromatography of viruses." Journal of Chromatography A, 1142 (2007), pp. 2-12. (Year: 2007).*

Fukazawa, et al. "Surface Modification of Various Materials Using Photoreactive MPC Polymer", Function & materials, 2013, vol. 33, No. 9, pp. 26-32 with English translation, 12 pages.

Takai, "Evaluation of Biocompatible Polymer for Medical Devices", Materials Science and Technology, 2015, vol. 52, No. 1, pp. 14-17 (3), with English translation.

English translation of the PCT Written Opinion of the International Searching Authority dated Aug. 1, 2017, International Application No. PCT/JP2017/019121, 9 pages.

Valadi, et al. "Exosome-mediated transfer of mRNAs and microRNAs is a novel mechanism of genetic exchange between cells", Nature Cell Biology, 2007, vol. 9, p. 654-659, 17 pages.

Skog, et al. "Glioblastoma Microvesicles Transport RNA and Protein that Promote Tumor Growth and Provide Diagnostic Biomarkers", 2008, Nat. Cell Biol. vol. 10, pp. 1470-1476, 16 pages.

Extended European Search Report dated Feb. 7, 2020, Application No. EP 17 80 2773, 44 pages.

Chinese Office Action dated Jun. 23, 2020, Application No. 201780032132.4, English translation included, 18 pages.

* cited by examiner

Figure 1

Figure 2 the amount recovered

CD63

CD9 the amount adsorbed

METHOD OF RECOVERING EXTRACELLULAR VESICLES AND CONTAINER FOR EXTRACELLULAR VESICLES

TECHNICAL FIELD

The present invention relates to a method for efficiently recovering cell-derived vesicles represented by exosomes, and a container and a tool for the recovery. Moreover, it relates to a substrate, channel or the like to use in methods for testing with exosomes.

BACKGROUND ART

Extracellular vesicles are vesicles originating from cells, present outside the cell, and classified as exosomes, microvesicles, apoptotic bodies depending on their size. Exosomes and microvesicles contain proteins and nucleic acids such as mRNA and miRNA, and apoptotic bodies contain fragmented nuclei and organelles. Among extracellular vesicles, since exosomes and microvesicles contain proteins and nucleic acids, they also contain information from the emitting cell, and thereby have the possibility to be used as biomarkers. Especially, exosomes include the possibility to be used as diagnostic markers and in treatments and have attracted attention in recent years.

Exosomes are vesicles with a diameter of 30 to 100 nm, formed by a lipid bilayer membrane secreted by the cell. Exosomes are known to be secreted by most cells and their presence has been confirmed in body fluids such as blood, saliva, urine and breast milk. Since exosomes contain RNA and proteins from the cell from which they were secreted, it has been suggested that they may transmit information to distant cells by circulating in body fluids (Non Patent Literature 1). It has been shown that the progress of cancer may be promoted by the nucleic acids and proteins contained in the exosomes from cancer cells, thereby the possibility of a establishing cancer diagnosis system using exosomes has been suggested (Non Patent Literature 2).

As mentioned above, it has been made clear that the proteins and nucleic acids contained in exosomes differ depending on the cell type they were secreted from. Therefore, the nucleic acids and proteins from exosomes are useful as diagnostic markers. Moreover, since exosomes are also contained in saliva and urine, it is possible to have a non-invasive diagnosis method if a testing method with high accuracy using exosomes can be established. Moreover, attempts are made to use exosomes taken and collected from healthy cells for the recovery of damaged cells or diseased cells, by using the information transmission function of exosomes (Patent Literature 1).

A purifying method with a good recovery rate is necessary to purify exosomes from a small amount of sample, such as saliva, or to purify a large amount of exosomes for therapeutic purposes. As conventional methods for purifying exosomes, methods for isolating them by centrifugal separation or columns are disclosed (Patent Literatures 2 and 3). Among these, centrifugal separation method using ultracentrifugation is an established recovery technique and is an excellent technique in that the shape of exosomes can be maintained.

For example, if recovering exosomes from the culture supernatant of cells, after removing cell debris from the culture medium containing the exosomes by low-speed centrifugation, the exosomes can be recovered as pellets by ultracentrifugation for about 2 h. The thus obtained exosomes can be redispersed in a buffer solution such as PBS and further purified, or directly used for analysis in tests, research and the like.

CITATION LIST

Patent Literature

Patent Literature 1: National Publication of International Patent Publication No. 2014-507140
Patent Literature 2: National Publication of International Patent Publication No. 2003-531864
Patent Literature 3: National Publication of International Patent Publication No. 2002-535665
Patent Literature 4: Japanese Patent Laid-Open No. 7-83923
Patent Literature 5: International Publication No. WO 2005/001019

Non Patent Literature

Non Patent Literature 1: Valadi, H. et al., 2007, Nat. Cell Biol., Vol. 9, p. 654-659.
Non Patent Literature 2: Skog, J. et al., 2008, Nat. Cell Biol., Vol. 10, pp. 1470-1476.

SUMMARY OF INVENTION

Technical Problem

However, in the above recovery method by ultracentrifugation, the problem was that the exosomes non-specifically adsorbed to the plastic surface of the recovery container that is used, and thus a stable recovery rate could not be obtained and the recovery rate decreased at each operation. Especially when performing quantitative analysis, the adsorption to the surface of the containers used for purification and of the analytical instruments influences not only the efficiency of the analysis, but also the analysis results. However, an effective method to prevent the adsorption of extracellular vesicles such as exosomes has not yet been developed.

A method for preventing proteins, which are tissue-derived biomaterials, and cells to non-specifically adsorb to the container by a hydrophilic polymer, is disclosed (Patent Literatures 4 and 5). Patent Literature 4 discloses that the adsorption of proteins can be prevented by coating a polystyrene container with a PBS solution containing a 2-methacryloyloxyethyl phosphorylcholine polymer or a copolymer of a component containing 2-methacryloyloxyethyl phosphorylcholine. Patent Literature 5 discloses that the adhesion of ES cells to the culture vessel can be prevented and the embryoid body can be formed efficiently, by covering the culture vessel using a compound containing a phosphorylcholine analogous group.

However, in Patent Literature 4, the method is specific to proteins, and although proteins appear on the surface of exosomes etc., it was difficult to completely prevent the adsorption of the extracellular vesicles formed by a lipid bilayer membrane. Moreover, the method in Patent Literature 5 prevents the adsorption of cells formed by a lipid bilayer membrane, but between cells and extracellular vesicles, especially exosomes, their size is completely different, and thus the degree of adsorption to the container is significantly different, so that the adsorption of the exosomes to the container could not be completely prevented.

The present invention aims to provide a coating agent to prevent the adsorption of cell-derived vesicles to the container used for purification such as a centrifuge tube or to tools such as pipette chips, when purifying cell-derived vesicles represented by exosomes, and to improve the recovery rate. Moreover, it aims to provide a coating agent that not only can be used during the purification process, but also can improve the accuracy of exosome analysis by coating the substrates, channels or the like used for exosome analysis. Furthermore, it aims to provide containers or analytical tools such as a chip or a substrate coated with these coating agents.

Solution to Problem

The present invention relates to the following coating agents, tools, purification methods and analysis methods.
(1) A coating agent for preventing the adsorption of extracellular vesicles, comprising: a hydrophilic polymer having a weight average molecular weight of 10,000 or more and 1,000,000 or less, wherein a coated layer formed by the coating agent has a contact angle of 0 degree or more and 30 degrees or less.
(2) The coating agent according to (1), wherein the hydrophilic polymer comprises one or more hydrophilic monomers of 2-methacryloyloxyethyl phosphorylcholine, vinyl alcohol, vinylpyrrolidone, methoxy alkylene glycol monomethacrylate and 2-hydroxyethyl methacrylate.
(3) The coating agent according to (2), wherein the hydrophilic monomer constituting the hydrophilic polymer is 2-methacryloyloxyethyl phosphorylcholine, and wherein the coating agent is a copolymer containing 30 mol % or more and 50 mol % or less of constituting unit based on 2-methacryloyloxyethyl phosphorylcholine, with the balance being a hydrophobic group-containing monomer.
(4) A tool coated with the coating agent according to any one of (1) to (3).
(5) A method for purifying and/or analyzing extracellular vesicles using the tool according to (4).

DESCRIPTION OF EMBODIMENTS

In the present invention, an extracellular vesicle means a vesicle derived from a cell, and concretely, refers to exosomes, microvesicles and apoptotic bodies. The following embodiments focus mainly on exosomes, but it is needless to say that they can also be applied to extracellular vesicles other than exosomes.

Moreover, by coating the tools used for the purification of extracellular vesicles like exosomes, such as centrifuge tubes, tubes and pipette chips with the coating agent of the present invention, it can prevent their adsorption and improve the recovery rate. Moreover, by coating analytical tools and analytical instruments used in this field, such as beads, micro-titer plates, slide glass, micro-TAS and lab-on-a-chip with it, it can prevent nonspecific adsorption and improve the analytical precision.

Tools of any materials can be coated with the coating agent of the present invention. For example, by coating polycarbonate, polypropylene and polyallomer that are often used for centrifuge tubes, vinyl chloride, polystyrene, polyethylene terephthalate, silicon, hydrophilic polydimethylsiloxane, hydrophobic polydimethylsiloxane, glass and metals such as stainless and aluminum that are used as base materials for analytical tools, with the coating agent of the present invention, the adsorption of extracellular vesicles such as exosomes can be prevented.

The contact angle of the coated layer obtained by the coating agent of the present invention is 0 degree or more and 30 degrees or less, and it is preferable that it be 0 degree or more and 25 degrees or less. Moreover, regarding the molecular weight of the hydrophilic polymer of the present invention, the weight average molecular weight is 10,000 or more and 1,000,000 or less, and in terms of durability of the coated layer, 100,000 or more is preferable, and it is more preferable to be 700,000 or less to suppress coating unevenness due to the high viscosity during coating.

Moreover, the hydrophilic monomer constituting the hydrophilic polymer can be any hydrophilic monomer as long as it can synthesize a hydrophilic polymer or copolymer, and among these, it is preferable that it be 2-methacryloyloxyethyl phosphorylcholine, vinyl alcohol, vinylpyrrolidone, methoxy alkylene glycol monomethacrylate or 2-hydroxyethyl methacrylate. These hydrophilic monomers may be used as a polymer, or may be used as a copolymer with another monomer.

Among these, the copolymer of 2-methacryloyloxyethyl phosphorylcholine (MPC) and a hydrophobic monomer can be used preferably. As the hydrophobic monomer, methyl methacrylate (MMA), n-butyl methacrylate (BMA), 2-ethylhexyl methacrylate (EhMA), dodecyl methacrylate (DMA), stearyl methacrylate (SMA), etc. can be used, and the copolymer with n-butyl methacrylate is particularly preferable in terms of availability and film-forming properties. Moreover, when preparing a copolymer of MPC and a hydrophobic monomer, the composition ratio of MPC and the hydrophobic monomer should be 20/80 to 50/50.

The coating agent of the present invention can be used as a solution containing the above polymer or copolymer in a concentration of 0.05% or more and 5.0% or less. The desired effect cannot be produced when it is less than 0.05 weight %, and a reduction of the effect due to the coating unevenness of the coating agent and the physical peeling of the coating agent may occur when it is more than 5 weight %. As the solvent, alcohols such as ethanol and methanol, or buffer solutions conventionally used in this field such as a phosphate buffer solution, a tris buffer solution, PBS or TBS can be used.

Moreover, the coated layer thickness when forming a coated layer on a tool with the coating agent, is preferably 50 nm or more and 2000 nm or less, and more preferably, is preferably 90 nm or more and 900 nm or less.

When forming a coated layer on a tool, it is not possible to form the coated layer completely evenly. Since it is very difficult to form a coated layer with a thin thickness, when the average thickness is less than 50 nm, the variation of the coated layer thickness increases and spots where the effect preventing the adsorption of the exosomes is weak are generated. Moreover, when the coated layer thickness is greater than 2000 nm, the viscosity of the coating liquid (polymer solution) used to form the coated layer increases and the amount of polymer used also increases, making it difficult in terms of work efficiency during coated layer forming (in terms of drying and operability) and economic efficiency. If the coated layer thickness is 50 nm or more and 2000 nm or less, it is effective to prevent the adsorption of exosomes. Moreover, when the coated layer thickness is 90 nm or more and 900 nm or less, the adsorption of exosomes can be prevented and stable measurement results can be obtained since the coated layer can be formed at a stable thickness.

The present invention is described below in details while showing examples.

1. Polymer

In the following examples, the polymers shown in the following Table 1 were used.

Polymer 1

MPC (23.5 g) and BMA (26.5 g) were dissolved in ethanol (50 g) and placed in a four-neck flask, nitrogen was bubbled for 30 min, then t-butyl peroxyneodecanoate (0.1 g) was added at 45° C. and the polymerization reaction was performed for 24 h. The polymerization liquid was added dropwise to 3 L of diethyl ether while stirring, the precipitate was filtered, then dried in vacuum for 48 h at 45° C., to obtain 36.8 g of powder. The molecular weight was measured by gel permeation chromatography (manufactured by Tosoh Corporation) using polyethylene glycol as the standard. The weight-average molecular weight was 580,000. An analysis of the composition by $^1$H-NMR showed that MPC/BMA=30/70 (mole ratio).

The above polymer (0.5 g) was dissolved in ethanol (100 g) to prepare a solution of 0.5 weight %. After applying this on a PET film, it was air-dried and washed with water. This was used as the sample for measuring the contact angle. The contact angle measurement was performed by the bubble method using a DropMaster (manufactured by Kyowa Interface Science Co., LTD.) and the value of the contact angle was obtained as the water's contact angle. Concretely, it was calculated as "180°−bubble angle". The value of the contact angle for the coated layer obtained was 25 degrees.

Polymer 2

MPC (4.7 g) and BMA (5.3 g) were dissolved in ethanol (90 g) and placed in a four-neck flask, nitrogen was bubbled for 30 min, then t-butyl peroxyneodecanoate (0.25 g) was added at 60° C. and the polymerization reaction was performed for 24 h. The polymerization liquid was added dropwise to 3 L of diethyl ether while stirring, the precipitate was filtered, then dried in vacuum for 48 h at 45° C., to obtain 36.8 g of powder. The weight-average molecular weight was 120,000. An analysis of the composition by $^1$H-NMR showed that MPC/BMA=30/70 (mole ratio). The value of the contact angle for the coated layer obtained was 20 degrees.

Polymer 3

Poly(2-hydroxyethyl methacrylate) with a molecular weight of 300,000 (manufactured by Sigma-Aldrich) was used for polymer 3. The value of the contact angle for the coated layer obtained was 30 degrees.

[Polymer 4] (Comparative Example)

For polymer 4, 8.4 g of MPC and 36.6 g of BMA were dissolved in 54.6 g of ethanol and placed in a four-neck flask, nitrogen was bubbled for 30 min, then 0.37 g of t-butyl peroxyneodecanoate was added at 60° C. and the polymerization reaction was performed for 24 h. The polymerization liquid was added dropwise to 3 L of diethyl ether while stirring, the precipitate was filtered, then dried in vacuum for 48 h at 45° C., to obtain 26.3 g of powder. The weight-average molecular weight was 340,000. An analysis of the composition by $^1$H-NMR showed that MPC/BMA=10/90 (mole ratio). The value of the contact angle for the coated layer obtained was 42 degrees.

TABLE 1

| | Composition | Composition ratio (mole ratio) | Weight-average molecular weight | Contact angle |
|---|---|---|---|---|
| Polymer 1 | MPC/BMA | 30/70 | 580,000 | 25 |
| Polymer 2 | MPC/BMA | 30/70 | 120,000 | 20 |
| Polymer 3 | HEMA | 100 | 300,000 | 30 |
| Polymer 4 | MPC/BMA | 10/90 | 340,000 | 42 |

The coating of the container used for purification was performed by using the coating agent containing the above hydrophilic polymers, and the analysis of the amount of exosome adsorbed was performed. For the coating, the container surface was wetted with an ethanol solution containing 0.5 wt % of each hydrophilic polymer, i.e. polymers 1 to 3 and polymer 4, that is the comparative example, shown in Table 1, then dried after eliminating the excess liquid.

2. Comparison of the Adsorption of Exosomes According to the Presence or Absence of the Hydrophilic Polymer

[Preparation of the Culture Supernatant Containing the Exosomes]

The exosomes were obtained from the culture supernatant of HuH-7 cells derived from human liver cancer, or HT-29 cells derived from colon cancer. The following was performed to obtain exosomes from HuH-7 cells. HuH-7 cells ($1\times10^6$) were suspended in 25 mL of RPMI-1640 medium supplemented with 10% fetal bovine serum (manufactured by Thermo Fisher Scientific Inc.) and $\frac{1}{100}$ of penicillin-streptomycin (Penicillin-Streptomycin Solution ×100, manufactured by Wako Pure Chemical Industries, Ltd.), then seeded in a 150 mm petri dish (cell culture dishes 150 mm, manufactured by IWAKI & CO., LTD.) and cultured in 5% $CO_2$, at 37° C. for 72 h. Then, the medium was sucked and removed, 25 mL of RPMI-1640 medium without fetal bovine serum was added and cultured in 5% $CO_2$, at 37° C. for 66 h. After 66 h, the culture supernatant was recovered, subjected to low-speed centrifugation at 8,900×g for 10 min, and the supernatant was passed through a 0.22 μm filter (milliex-GS SLGV033RS, manufactured by Merck).

The following was performed to obtain exosomes from HT-29 cells. HT-29 cells ($2\times10^8$) were seeded in 500 mL of McCoy's 5A medium supplemented with 10% fetal bovine serum and penicillin-streptomycin and cultured in 5% $CO_2$, at 37° C. for 96 h, using a Bellocell incubator (manufactured by CESCO). Next, the medium was removed by decantation, 500 mL of McCoy's 5A medium without fetal bovine serum was added and further cultured in 5% $CO_2$, at 37° C. for 72 h. After 72 h, the culture supernatant was recovered, subjected to low-speed centrifugation as above, and the culture supernatant containing the exosomes was obtained by passing the supernatant through the filter.

[Example 1] Exosome Adsorption Experiment 1

Concentration of the exosomes was performed by centrifuging 480 mL of culture supernatant of HuH-7 cells prepared above at 30,700 rpm for 70 min. The precipitate was resuspended in 12 mL of culture supernatant and 60 mL of culture supernatant was further added to obtain a sample in which the exosomes were concentrated.

In the following ultracentrifugation step, the samples containing the exosomes were dispensed in equal amounts in tubes for ultracentrifugation (UC tube, Ultra-Clear Tubes, manufactured by Beckman Coulter, Inc.) coated with the coating agents, each containing polymer 1 as the hydrophilic polymer, or an uncoated centrifuge tubes, and the purification was performed, then the exosome recovery rate was compared according to the presence or absence of the coating agent. The coated layer thickness of the coating agent used in the following experiments was about 90 nm unless otherwise stated.

The sample containing the concentrated exosomes was centrifuged at 30,700 rpm for 120 min. The obtained precipitate was suspended by pipetting in 3 mL of 45% OptiPrep (manufactured by COSMO BIO CO., LTD.), centrifuged at 24,200 rpm for 20 min using a 8-40% gradient, then collected in 10 fractions. Each collected fraction was centrifuged at 30,700 rpm for 120 min, the precipitate was suspended in 250 µL of PBS and then recovered.

The exosomes recovered in each fraction and the amount of exosome adsorbed on the centrifuge tube was analyzed by western blotting. Western blotting was performed according to a conventional method, and CD9 and CD63, which are known as exosome markers, were detected. Anti-CD9 antibodies and anti-CD63 antibodies (both manufactured by COSMO BIO CO., LTD.) were reacted each as primary antibodies with HRP-labeled anti-mouse IgG antibodies (manufactured by Bio-Rad Laboratories, Inc.) as secondary antibodies and chemiluminescence detection was performed.

Figure 1:
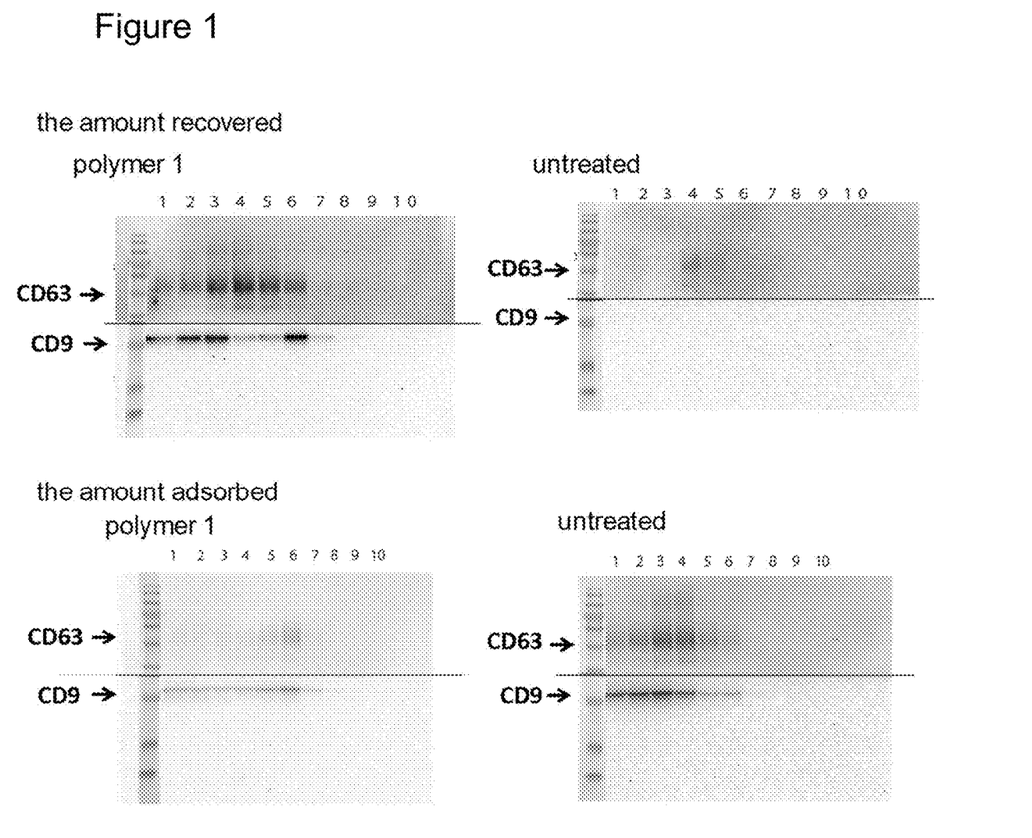
FIG. 1 is a drawing showing the amount of exosomes recovered according to the presence or absence of the coating agent.

FIG. 1 is a comparison of the amount of exosome recovered (the amount recovered) in each fraction fractionated in 10 fractions and the amount of exosome that was adsorbed to the centrifuge tube and could not be recovered (the amount adsorbed) when using the coating agent containing polymer 1 as the hydrophilic polymer or an untreated centrifuge tube. As shown in FIG. 1, when performing the purification of exosomes without using the coating agent, the amount of exosome recovered was very small and many of the exosomes were adsorbed to the centrifuge tube. By contrast, when performing the purification using a centrifuge tube coated with polymer 1 as the hydrophilic polymer, the amount of exosome adsorbed to the centrifuge tube was very small and most of the exosomes could be resuspended and recovered.

[Example 2] Exosome Adsorption Experiment 2

A sample in which 23 mL of PBS was added to 12 mL of culture supernatant of HuH-7 cells which were filtered through a 0.22 µm filter after low-speed centrifugation as above, was placed in a centrifuge tube coated with the polymers 1 to 3 as the hydrophilic polymer, or an untreated centrifuge tube, and was subjected to ultracentrifugation at 37,000 rpm for 70 min. The precipitate was suspended in 250 µL of PBS and recovered. The centrifuge tube after recovering the precipitate was eluted by adding 150 µL of 1×SDS sample buffer (first centrifuge tube adsorption sample). 30 mL of PBS was added to the recovered exosomes and the mixture was subjected to centrifugation again at 37,000 rpm for 120 min, using a new centrifuge tube coated with polymers 1 to 3 as the hydrophilic polymer, or a new untreated centrifuge tube. The exosomes were recovered by suspending them with PBS to amount to 150 µL. Then, the centrifuge tube after recovering the exosomes was eluted by adding 150 µL of 1×SDS sample buffer (second centrifuge tube adsorption sample).

The recovered exosomes and the exosomes adsorbed to the centrifuge tube at the first and second ultracentrifugation were analyzed by western blotting in the same manner as in Example 1. The results are shown in FIG. 2.

Figure 2:
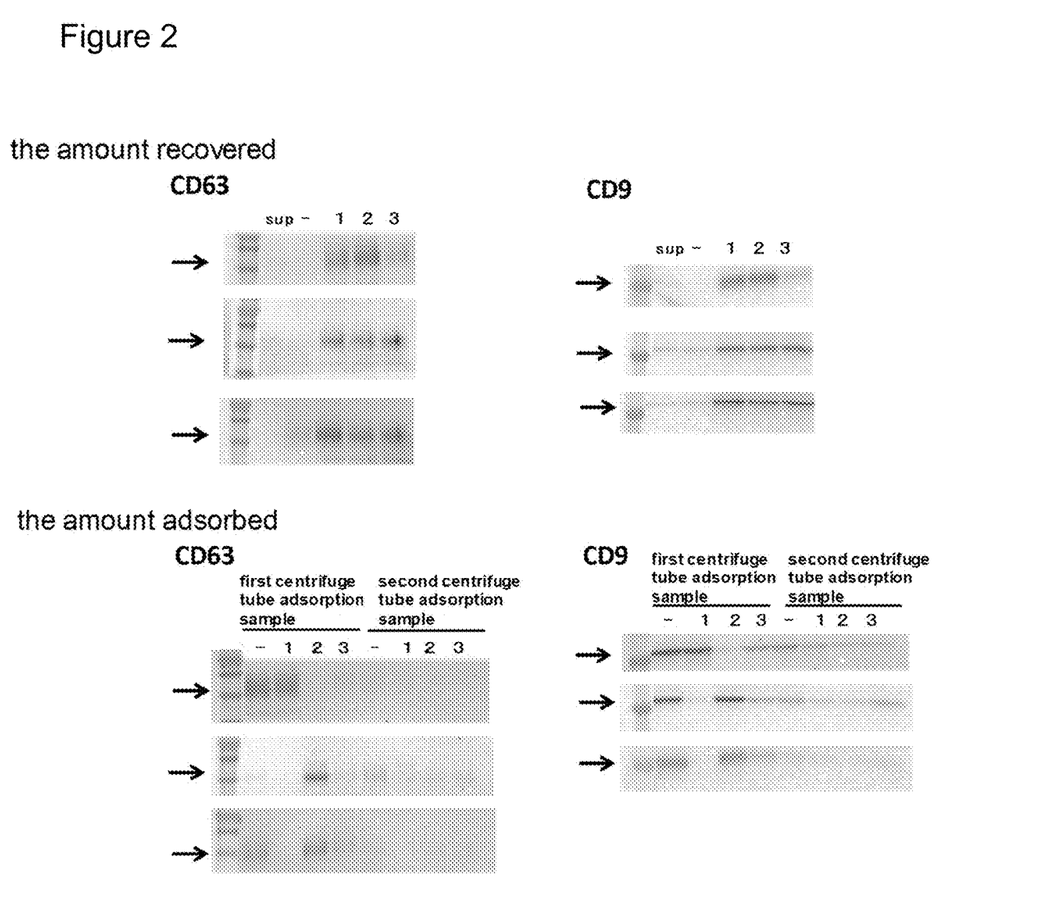
FIG. 2 is a drawing showing the amount of exosomes recovered according to the type of coating agent.

The same experiment was performed 3 times and FIG. 2 shows the results of the western blotting for each experiment. In the drawing, supernatant (sup) indicates that the culture supernatant was used,—the untreated centrifuge tube, and 1 to 3 the centrifuge tubes coated with the coating agent containing polymers 1 to 3 as the hydrophilic polymer.

In either instance detecting the marker CD63 or CD9, the exosomes were efficiently recovered when using the coating agent. On the other hand, when using the untreated (-) centrifuge tube, the amount of exosome adsorbed nonspecifically to the centrifuge tube increases and the recovery rate greatly decreases.

[Example 3] Exosome Adsorption Experiment 3

Figure 3:
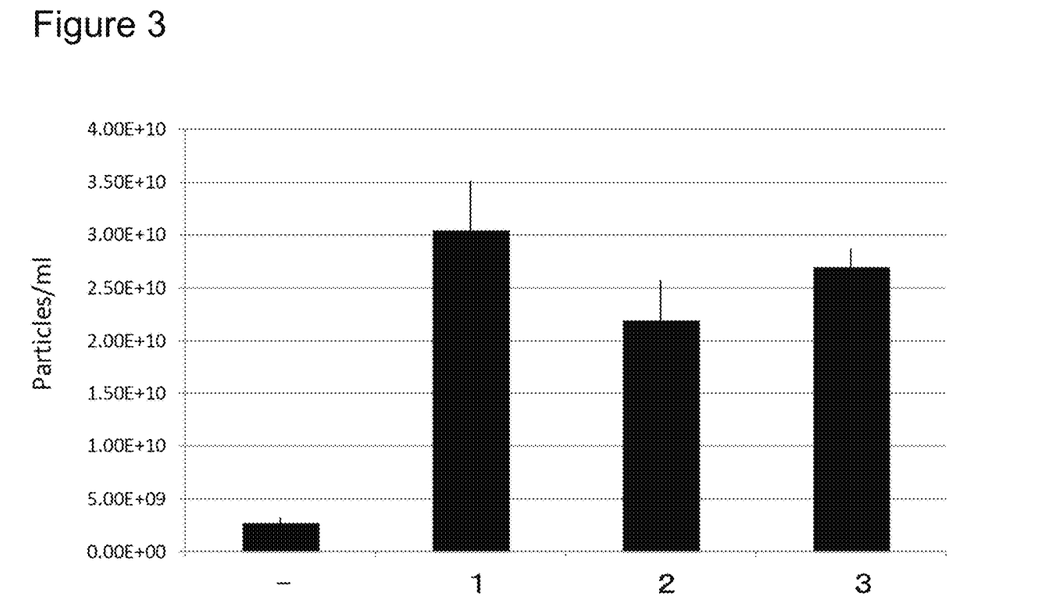
FIG. 3 is a drawing showing the results of examining the amount of exosomes recovered according to the coating agent by the number of particles.

The number of particles of exosome recovered in Example 2 was measured with NanoSight LM10 (manufactured by Malvern Panalytical Ltd.). The calibration was performed with Silica Microspheres: 100 nm (Polysiciences, Inc. #24041) diluted with Milli-Q water passed through a GE Puradisc 13 (NYL 0.1 µm). Next, the exosomes were diluted to approximately $10^8$ with PBS passed through a GE Puradisc 13, the sample solution was injected in the measurement cell with a syringe and waited 10 s, then data measurement for 30 s was performed. The measurement was performed 5 times while replacing the inside of the cell with a new sample, by pushing the syringe and moving the sample solution in the chamber. FIG. 3 shows the average value with standard deviation. The Detection threshold was 4 and the Camera level was 14.

It is clear that the recovery rate of the exosomes greatly improves compared to when performing the purification using an untreated centrifuge tube, in all instances using the coating agent containing either hydrophilic polymers, polymers 1 to 3.

Example 4

Centrifugation was performed once or twice as below, and the amount of exosome recovered and the amount adsorbed to the tube were examined. The exosomes were purified as below from the culture supernatant of HT-29 cells. The culture supernatant (500 mL) of HT-29 cells prepared as above was centrifuged at 160,000×g for 70 min to precipitate the exosomes, then the precipitate was resuspended in 180 mL of PBS, and further centrifuged at 160,000×g for 70 min and washed. The obtained precipitate was resuspended in 1.3 mL of PBS, to form an exosome crude fraction.

The exosome crude fraction (1.3 mL) was mixed with 1.7 mL of 46% Iodixanol (OptiPrep, manufactured by COSMO BIO CO., LTD.) and placed on the bottom of a centrifuge tube, then 8% to 40% of Iodixanol continuous density gradient was superposed on top of it. Equilibrium density gradient centrifugation was performed at 100,000×g for 17 h in the centrifuge tube by a Beckman L-90K centrifuge with a SW 32 Ti rotor. After centrifugation, 3 fractions of 4.26 mL each were recovered from the upper liquid surface of the sample, then 6 fractions of 3.26 mL each were recovered, dividing it into a total of 9 fractions. Each fraction was suspended in 27 mL of PBS and centrifuged at 160,000×g for 120 min, then the precipitate was suspended in 500 µL of PBS to obtain the purified exosomes. Of these 9 fractions, fraction 2 (density: 1.36 g/cm$^3$) was used as the purified exosome sample in this experiment.

The exosome solution (30 µL) of a density of 1.36 g/cm$^3$ obtained from the culture supernatant of HT-29 cells was each placed in microtubes (manufactured by Eppendorf AG). Tubes coated in advance with the hydrophilic polymers, polymer 1 or polymer 4 were prepared. For the adsorption experiment, it was allowed to stand still for 10 min, then after centrifuging at 13,200 rpm at 4° C. for 30 min, it was stirred for 10 s with a vortex mixer and the exosomes were recovered. If performing the centrifugation twice, the exosomes were recovered after performing the same step twice. Regarding the recovered exosomes was analyzed by western blotting, and the number of particles was examined using a NanoSight LM10. The experiment was performed three times, and the average number of particles and the results of the three experiments by western blotting are shown (FIG. 4).

Figure 4A:
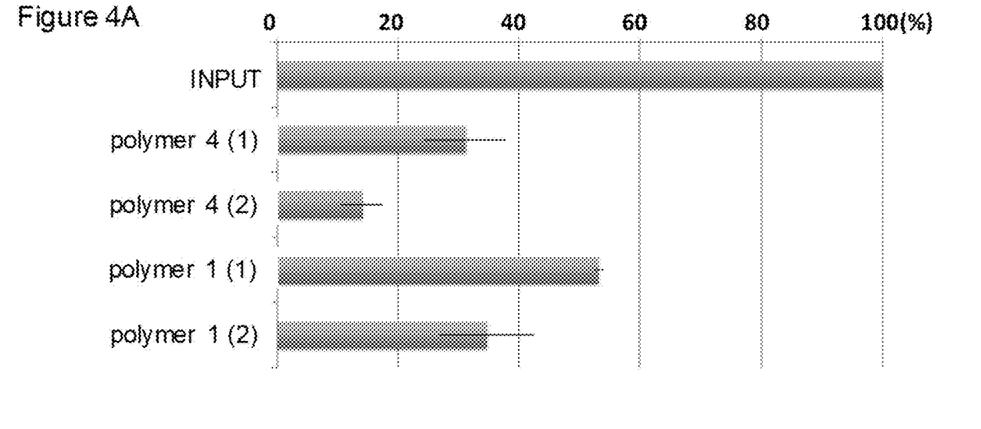
FIG. 4A is a drawing showing the results of examining the amount of exosomes recovered according to the coating agent by the number of particles, and FIG. 4B by western blotting.

FIG. 4A shows the analysis results of the number of particles of exosomes recovered. The average value of the three experiments is shown as the ratio to the input, and the numbers between parentheses show the number of centrifugations. When using polymer 1, 50% or more of the particles to the input can be recovered when performing the centrifugation once, and 30% or more even when performing the centrifugation twice. By contrast, when using the Comparative Example, polymer 4, the recovery rate was only 30% when performing the centrifugation once, and 15% when performing it twice.

Figure 4B:
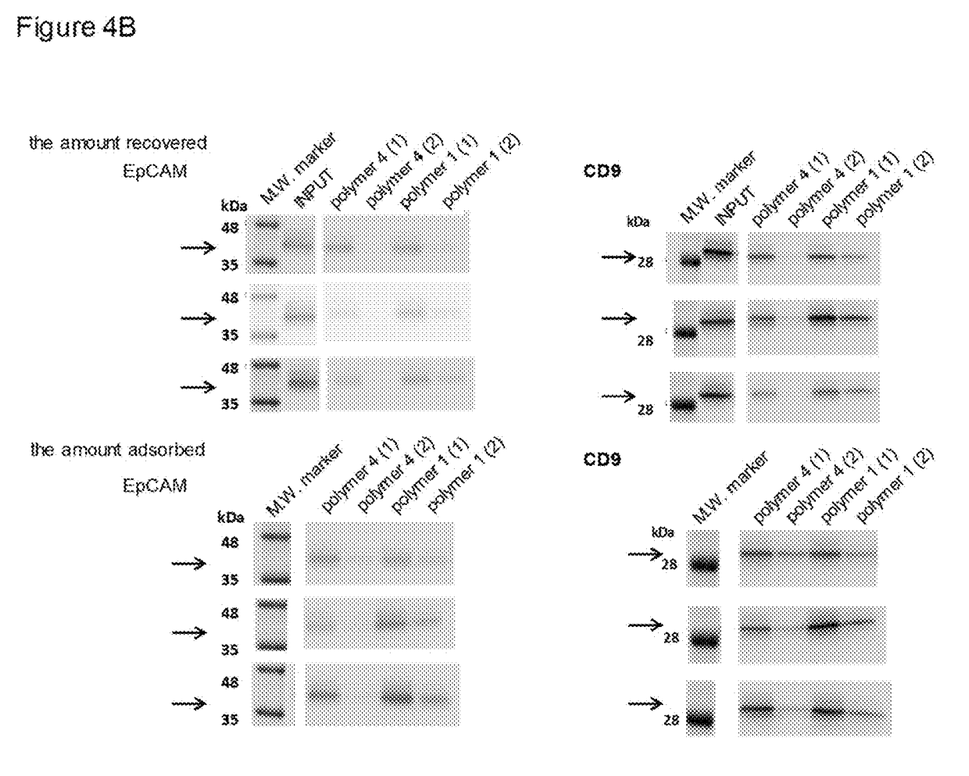

FIG. 4B shows the results of the analysis by western blotting. The recovered samples and the samples adsorbed to the tube in the first, second and third experiments were analyzed, and each panel shows the analysis results of the first experiment to the third experiment in this order from the top. Detection was performed using anti-EpCAM antibodies (manufactured by R&D Systems, Inc.) and anti-CD9 antibodies. When using polymer 4, with the sample recovered after performing the centrifugation twice, almost nothing was detected when using either anti-EpCAM antibodies or anti-CD9 antibodies, but when using polymer 1, it was detectable in both cases.

Example 5

A comparison of the amount adsorbed according to the coated layer thickness of the coating agent was conducted. Polymer 1 was dissolved in ethanol so as to be 0.5, 1.0, 2.0 and 4.0 wt % and then microtubes (manufactured by Treff AG) were coated with them changing the coated layer thickness from 90 nm to 1400 nm, to use for the analysis. The coated layer thickness was measured using a reflection spectroscopic film thickness meter (FE-3000, manufactured by OTSUKA ELECTRONICS Co., LTD.). As in Example 4, the amount of exosomes recovered was compared by using the exosomes obtained from the culture supernatant of HT-29 cells and performing centrifugation once or twice.

Figure 5A:
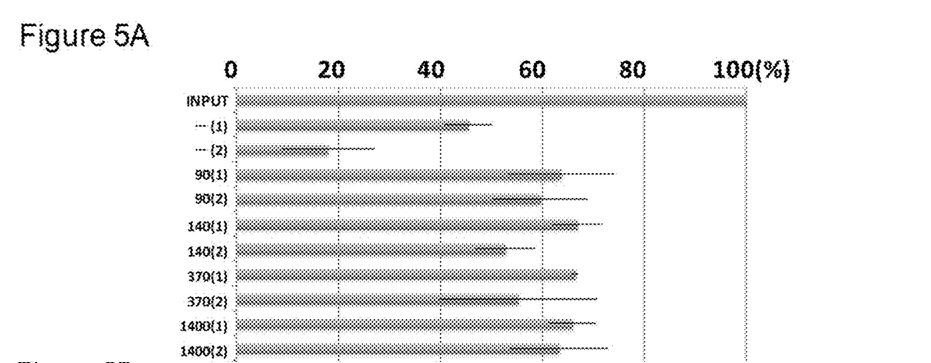
FIG. 5A is a drawing showing the results of examining the amount of exosomes recovered according to the coated layer thickness of the coating agent by the number of particles.

FIG. 5A shows the analysis results of the number of particles of exosomes recovered. The numbers 90, 140, 370 and 1400, that are shown on the left, indicate the thickness (nm) of the coated layer with which the microtubes were coated. The average value of the three experiments is shown as the ratio to the input, and the numbers between parentheses show the number of centrifugations. A symbol, -, indicates the results when using an untreated tube. With either coated layer thickness, when using a coated tube, 50% or more of the particles to the input could be recovered. By contrast, with the untreated tube, only approximately 45% on average of the particles could be recovered when performing the centrifugation once, and 20% or less on average when performing the centrifugation twice.

No difference between the amounts recovered according to the thickness of the coating agent was observed in the analysis of the number of particles, but it is preferable to be a coated layer thickness of 50 nm or more and 2000 nm or less when considering the variation during the coated layer formation and the work efficiency. If the coated layer thickness is within this range, the adsorption of exosomes should be prevented and stable measurement results should be obtained.

Figure 5B:
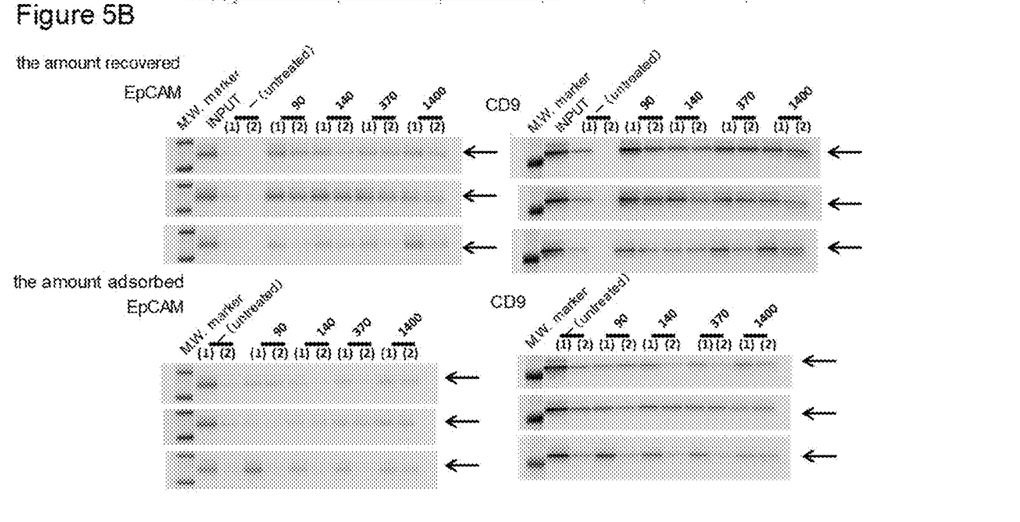
FIG. 5B is a drawing analyzing the results by western blotting.

FIG. 5B shows the results of the analysis by western blotting. As in Example 4, it shows the results of the detection by anti-EpCAM antibodies and anti-CD9 antibodies. With either coated layer thickness, results clearly showing that the adsorption of exosomes can be suppressed compared to an uncoated tube, were obtained.

Figure 5C:
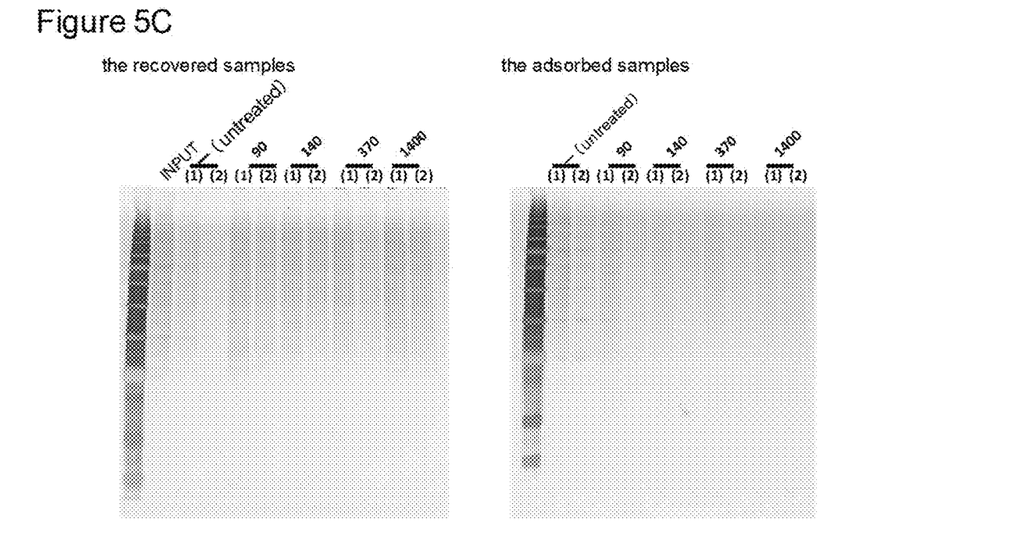
FIG. 5C is a drawing analyzing the recovered sample and adsorbed sample by electrophoresis and silver staining.

FIG. 5C shows the results of analysis of the recovered samples and the samples adsorbed to the tube by SDS electrophoresis and silver staining. When using an untreated tube, the amount recovered clearly decreases. By contrast, when performing coating with either coated layer thickness, it is clear that the adsorbed sample decreases and the recovered sample increases.

As shown in the above examples, the adsorption of exosomes to the container decreases and the recovery rate significantly improves, by using the coating agents containing polymers 1 to 3. These coating agents allow not only to improve the exosome recovery rate, but also to accurately perform quantitative analysis.

INDUSTRIAL APPLICABILITY

Using the coating agents of the present invention allows to prevent that extracellular vesicles including exosomes adsorb to the container, the substrate used in the analysis or the like. Thus, it allows to significantly improve the recovery rate of extracellular vesicles and also improve the accuracy of the analysis.

The invention claimed is:
1. A method for purifying extracellular vesicles, comprising:
   obtaining a culture medium containing exosomes,
   removing cell debris from the culture medium containing exosomes by low-speed centrifugation,
   performing an ultracentrifugation of the culture medium containing exosomes from which the cell debris has been removed, using a tool coated with a coating agent for preventing the adsorption of extracellular vesicles, and recovering exosomes by recovering precipitates in the tool after the ultracentrifugation, wherein the coating agent comprises a hydrophilic polymer having a weight average molecular weight of 10,000 or more and 1,000,000 or less, the hydrophilic polymer is a copolymer containing 30 mol % or more and 50 mol % or less of a hydrophilic monomer and the balance of a hydrophobic group-containing monomer, the hydrophilic monomer constituting the hydrophilic polymer is 2-methacryloyloxyethyl phosphorylcholine, and a coated layer formed by the coating agent has a contact angle of 0 degree or more and 30 degrees or less.

* * * * *